(12) United States Patent
Yoshizawa

(10) Patent No.: US 8,594,774 B2
(45) Date of Patent: Nov. 26, 2013

(54) SLEEP DETERMINATION DEVICE AND SLEEP DETERMINATION METHOD

(75) Inventor: Shintaro Yoshizawa, Gotemba (JP)

(73) Assignee: Toyota Jidosha Kabushiki Kaisha, Toyota-Shi (JP)

( * ) Notice: Subject to any disclaimer, the term of this patent is extended or adjusted under 35 U.S.C. 154(b) by 451 days.

(21) Appl. No.: 13/061,185

(22) PCT Filed: Aug. 27, 2009

(86) PCT No.: PCT/JP2009/064956
§ 371 (c)(1),
(2), (4) Date: Feb. 28, 2011

(87) PCT Pub. No.: WO2010/024329
PCT Pub. Date: Mar. 4, 2010

(65) Prior Publication Data
US 2011/0152704 A1  Jun. 23, 2011

(30) Foreign Application Priority Data
Sep. 1, 2008  (JP) ................... 2008-223536

(51) Int. Cl.
*A61B 5/04* (2006.01)

(52) U.S. Cl.
USPC ........................................ 600/509

(58) Field of Classification Search
USPC ........................................ 600/509
See application file for complete search history.

(56) References Cited

U.S. PATENT DOCUMENTS

| | | | |
|---|---|---|---|
| 7,623,912 B2 * | 11/2009 | Akselrod et al. | 600/513 |
| 8,078,269 B2 * | 12/2011 | Suzuki et al. | 600/513 |
| 2008/0242956 A1 * | 10/2008 | Suzuki et al. | 600/301 |

FOREIGN PATENT DOCUMENTS

| | | |
|---|---|---|
| CN | 1613425 A | 5/2005 |
| JP | 2004-358179 A | 12/2004 |
| JP | 2005-152310 A | 6/2005 |
| JP | 2005-304942 A | 11/2005 |
| JP | 2005-342200 A | 12/2005 |

(Continued)

OTHER PUBLICATIONS

Translation of International Preliminary Report on Patentability dated Apr. 12, 2011.

(Continued)

*Primary Examiner* — Christopher D Koharski
*Assistant Examiner* — Natasha Patel
(74) *Attorney, Agent, or Firm* — Kenyon & Kenyon LLP

(57) ABSTRACT

An object of the present invention is to provide a sleep determination device and a sleep determination method capable of precisely determining a sleep stage based on heartbeat information of a subject. The sleep determination device and the sleep determination method according to the present invention obtain the heartbeat of the subject, calculate a heartbeat cycle for each heartbeat based on the obtained heartbeat, calculate difference values until obtaining Nth-degree difference values set in advance with difference values between the successive heartbeat cycles as first-degree difference values and difference values between the successive first-degree difference values as second-degree difference values, generate a return map and a histogram indicative of a distribution of the respective values in a predetermined period of time for each of the heartbeat cycles and the difference values from the first-degree difference values to the Nth-degree difference values, and determine a sleep stage of the subject based on the generated return map and the histogram by referring to a return map and a histogram for determination set in advance for each sleep stage.

10 Claims, 9 Drawing Sheets

(56) References Cited

FOREIGN PATENT DOCUMENTS

| JP | 2006-102425 A | 4/2006 |
|---|---|---|
| JP | 2006-271474 A | 10/2006 |
| JP | 2007-229238 A | 9/2007 |
| JP | 2008-213595 A | 9/2008 |
| JP | 2010-057551 A | 3/2010 |
| JP | 2010-148605 A | 7/2010 |
| WO | 2004/107978 A1 | 12/2004 |

OTHER PUBLICATIONS

"Development of the drive dozing prevention technique using the sensor installed in the sheet for detecting the driver's condition"; Shigehiko Kaneko, Prof., Dept. of Mechanical Engineeering, the University of Tokyo; Masato Enokizono, Prof., Dept. of Electrical & Elecgronic Engineering, Oita University; Tsutomu Kamei, Director, Shimane Institute of Health Science; Etsunori Fujita, Managing Director, Delta Tooling Co., Ltd., Mar. 31, 2007.

Sosnowski, M., et al.: "Repeat Return Map Distinguishes Patients in the Chronic Phase after Myocardial Infarction with Different Risk for Future Cardiac Events"; Computers in Cardiology, 1995 IEEE, pp. 285-288.

\* cited by examiner

SLEEP DETERMINATION DEVICE AND SLEEP DETERMINATION METHOD

This is a 371 national phase application of PCT/JP2009/064956 filed 27 Aug. 2009, claiming priority to Japanese Patent Application No. JP 2008-223536 filed 1 Sep. 2008, the contents of which are incorporated herein by reference.

TECHNICAL FIELD

The present invention relates to a sleep determination device and a sleep determination method that determine a sleep stage of a subject.

BACKGROUND ART

Conventionally, as that which determines a sleep stage of a subject, that described in Japanese Unexamined Patent Application Publication No. 2005-152310 is known, which estimates a sleep stage based on the biological information about heartbeat fluctuation measured by a flow velocity or flow volume sensor of a fluid that flows through a vent section provided in an air mat, and body movement information. The purpose of the estimation device and the estimation method is to estimate a sleep stage of a subject who lies down on an air mat in an unrestrained state.

CITATION LIST

Patent Literature

Japanese Unexamined Patent Application Publication No. 2005-152310

SUMMARY OF INVENTION

Technical Problem

However, with such an estimation technique of a sleep stage, special equipment such as an air mat is required to estimate a sleep stage and it is also necessary to obtain body movement information. It is demanded to develop devices and methods capable of determining a sleep stage of a subject as precisely as possible only with heartbeat information even in the case where it is not possible to determine a sleep stage using special equipment, such as an air mat, or where body movement information cannot be obtained.

Hence, the present invention has been made in order to solve the above-mentioned problems and an object thereof is to provide a sleep determination device and a sleep determination method capable of precisely determining a sleep stage based on heartbeat information of a subject.

Solution to Problem

That is, a sleep determination device according to the present invention is configured to comprise a heartbeat obtaining unit that obtains a heartbeat of a subject; a difference calculating unit that calculates a heartbeat cycle for each heartbeat based on the heartbeat obtained by the heartbeat obtaining unit, and calculates difference values until obtaining Nth-degree difference values set in advance with difference values between the successive heartbeat cycles as first-degree difference values and difference values between the successive first-degree difference values as second-degree difference values; a distribution data generating unit that generates distribution data indicative of a distribution of the respective values in a predetermined period of time for each of the heartbeat cycles and the difference values from the first-degree difference values to the Nth-degree difference values calculated by the difference calculating unit; and a sleep determining unit that determines a sleep stage of the subject based on the distribution data generated by the distribution data generating unit by referring to distribution data for determination set in advance for each sleep stage.

According to the present invention, it is possible to discriminate the sleep stage of a subject in consideration of not only the fluctuation state of heartbeat cycles of the subject but also the fluctuation state of the fluctuation state etc. by calculating a heartbeat cycle for each heartbeat of the subject, calculating difference values until obtaining Nth-degree difference values set in advance with difference values between the successive heartbeat cycles as first-degree difference values and difference values between the successive first-degree difference values as second-degree difference values, generating distribution data indicative of a distribution of the respective values for each of the heartbeat cycles and the difference values from the first-degree difference values to the Nth-degree difference values, and determining a sleep stage of the subject based on the distribution data generated by the distribution data generating unit by referring to distribution data for determination set in advance for each sleep stage. Hence, it is possible to precisely determine a sleep stage of the subject based on heartbeat information.

In the sleep determination device according to the present invention, it is preferable for the distribution data generating unit to generate a return map that uses as parameters successive values of the heartbeat cycles and the difference values in a predetermined period of time for each of the heartbeat cycles and the difference values from the first-degree difference values to the Nth-degree difference values calculated by the difference calculating unit, and for the sleep determining unit to compare the return map generated by the distribution data generating unit with a return map for determination set in advance for each sleep stage to determine a sleep stage of the subject.

According to the present invention, it is possible to precisely discriminate the sleep stage of the subject based on the heartbeat cycle of the subject and the temporal change in the fluctuation state etc. by generating the return map that uses as parameters successive values of the heartbeat cycles and the difference values from the first-degree difference values to the Nth-degree difference values calculated by the difference calculating unit and by comparing the generated return map with a return map for determination set in advance for each sleep stage to determine a sleep stage of the subject.

In the sleep determination device according to the present invention, it is preferable for the sleep determining unit to set a return map for discrimination in advance in which the degree of separation is high in neighboring sleep stages and to compare the return map generated by the distribution data generating unit with the return map for discrimination to determine a sleep stage of the subject.

According to the present invention, it is possible to precisely discriminate the sleep stage of the subject by setting the return map for discrimination in advance in which the degree of separation is high in neighboring sleep stages and by comparing the return map generated by the distribution data generating unit with the return map for discrimination to determine a sleep stage of the subject.

In the sleep determination device according to the present invention, it is preferable for the distribution data generating unit to generate a histogram for each of the heartbeat cycles and the first-degree difference values to the Nth-degree difference values calculated by the difference calculating unit, and for the sleep determining unit to compare the histogram generated by the distribution data generating unit with a histogram for determination set in advance for each sleep stage to determine a sleep stage of the subject.

According to the present invention, it is possible to precisely discriminate the sleep stage of the subject in consideration of the heartbeat cycle of the subject and also statistical data such as the fluctuation state thereof, by generating the histogram for each of the heartbeat cycles and the difference values from the first-degree difference values to the Nth-degree difference values calculated by the difference calculating unit and by comparing the generated histogram with a histogram for determination set in advance for each sleep stage to determine a sleep stage of the subject.

In the sleep determination device according to the present invention, it is preferable for the sleep determining unit to set a histogram for discrimination in advance in which the degree of separation is high in neighboring sleep stages and to compare the histogram generated by the distribution data generating unit with the histogram for discrimination to determine a sleep stage of the subject.

According to the present invention, it is possible to precisely discriminate the sleep stage of the subject by setting a histogram for discrimination in advance in which the degree of separation is high in neighboring sleep stages as a histogram for determination and by comparing the histogram generated by the distribution data generating unit with the histogram for discrimination to determine a sleep stage of the subject.

The sleep determination method according to the present invention is configured to comprise a heartbeat obtaining step of obtaining a heartbeat of a subject; a difference calculating step of calculating a heartbeat cycle for each heartbeat based on the heartbeat obtained in the heartbeat obtaining step, and calculating difference values until obtaining Nth-degree difference values set in advance with difference values between the successive heartbeat cycles as first-degree difference values and difference values between the successive first-degree difference values as second-degree difference values; a distribution data generating step of generating distribution data indicative of a distribution of the respective values in a predetermined period of time for each of the heartbeat cycles and the difference values from the first-degree difference values to the Nth-degree difference values calculated in the difference calculating step; and a sleep determining step of determining a sleep stage of the subject based on the distribution data generated in the distribution generating step by referring to distribution data for determination set in advance for each sleep stage.

According to the present invention, it is possible to discriminate the sleep stage of a subject in consideration of not only the fluctuation state of heartbeat cycles of the subject but also the fluctuation state of the fluctuation state etc. by calculating a heartbeat cycle for each heartbeat of the subject, calculating difference values until obtaining Nth-degree difference values set in advance with difference values between the successive heartbeat cycles as first-degree difference values and difference values between the successive first-degree difference values as second-degree difference values, generating distribution data indicative of a distribution of the respective values for each of the heartbeat cycles and the difference values from the first-degree difference values to the Nth-degree difference values, and determining a sleep stage of the subject based on the distribution data generated by the distribution data generating unit by referring to distribution data for determination set in advance for each sleep stage. Hence, it is possible to precisely determine a sleep stage of the subject.

In the sleep determination method according to the present invention, it is preferable for the distribution data generating step to generate a return map that uses as parameters successive values of the heartbeat cycles and the difference values in a predetermined period of time for each of the heartbeat cycles and the difference values from the first-degree difference values to the Nth-degree difference values calculated in the difference calculating step, and for the sleep determining step to compare the return map generated in the distribution data generating step with a return map for determination set in advance for each sleep stage to determine a sleep stage of the subject.

According to the present invention, it is possible to precisely discriminate the sleep stage of the subject based on the heartbeat cycle of the subject and the temporal change in the fluctuation state etc. by generating the return map that uses as parameters successive values of the heartbeat cycles and the difference values from the first-degree difference values to the Nth-degree difference values calculated in the difference calculating step and by comparing the generated return map with a return map for determination set in advance for each sleep stage to determine a sleep stage of the subject.

In the sleep determination method according to the present invention, it is preferable for the sleep determining step to set a return map for discrimination in advance in which the degree of separation is high in neighboring sleep stages, and to compare the return map generated in the distribution data generating step with the return map for discrimination to determine a sleep stage of the subject.

According to the present invention, it is possible to precisely discriminate the sleep stage of the subject by setting the return map for discrimination in advance in which the degree of separation is high in neighboring sleep stages and by comparing the return map generated by the distribution data generating unit with the return map for discrimination to determine a sleep stage of the subject.

In the sleep determination method according to the present invention, it is preferable for the distribution data generating step to generate a histogram for each of the heartbeat cycles and the first-degree difference values to the Nth-degree difference values calculated by the difference calculating unit, and for the sleep determining step to compare the histogram generated in the distribution data generating step with a histogram for determination set in advance for each sleep stage to determine a sleep stage of the subject.

According to the present invention, it is possible to precisely discriminate the sleep stage of the subject in consideration of the heartbeat cycle of the subject and also statistical data such as the fluctuation state thereof, by generating the histogram for each of the heartbeat cycles and the difference values from the first-degree difference values to the Nth-degree difference values calculated by the difference calculating step and by comparing the generated histogram with a histogram for determination set in advance for each sleep stage to determine a sleep stage of the subject.

In the sleep determination method according to the present invention, it is preferable for the sleep determining step to set a histogram for discrimination in advance in which the degree of separation is high in neighboring sleep stages and to compare the histogram generated by the distribution data generating unit with the histogram for discrimination to determine a sleep stage of the subject.

According to the present invention, it is possible to precisely discriminate the sleep stage of the subject by setting a histogram for discrimination in advance in which the degree of separation is high in neighboring sleep stages as a histogram for determination and by comparing the histogram generated by the distribution data generating unit and the histogram for discrimination to determine a sleep stage of the subject.

Advantageous Effects of Invention

According to the present invention, it is possible to precisely determine a sleep stage of a subject based on heartbeat information of the subject.

Figure 1:
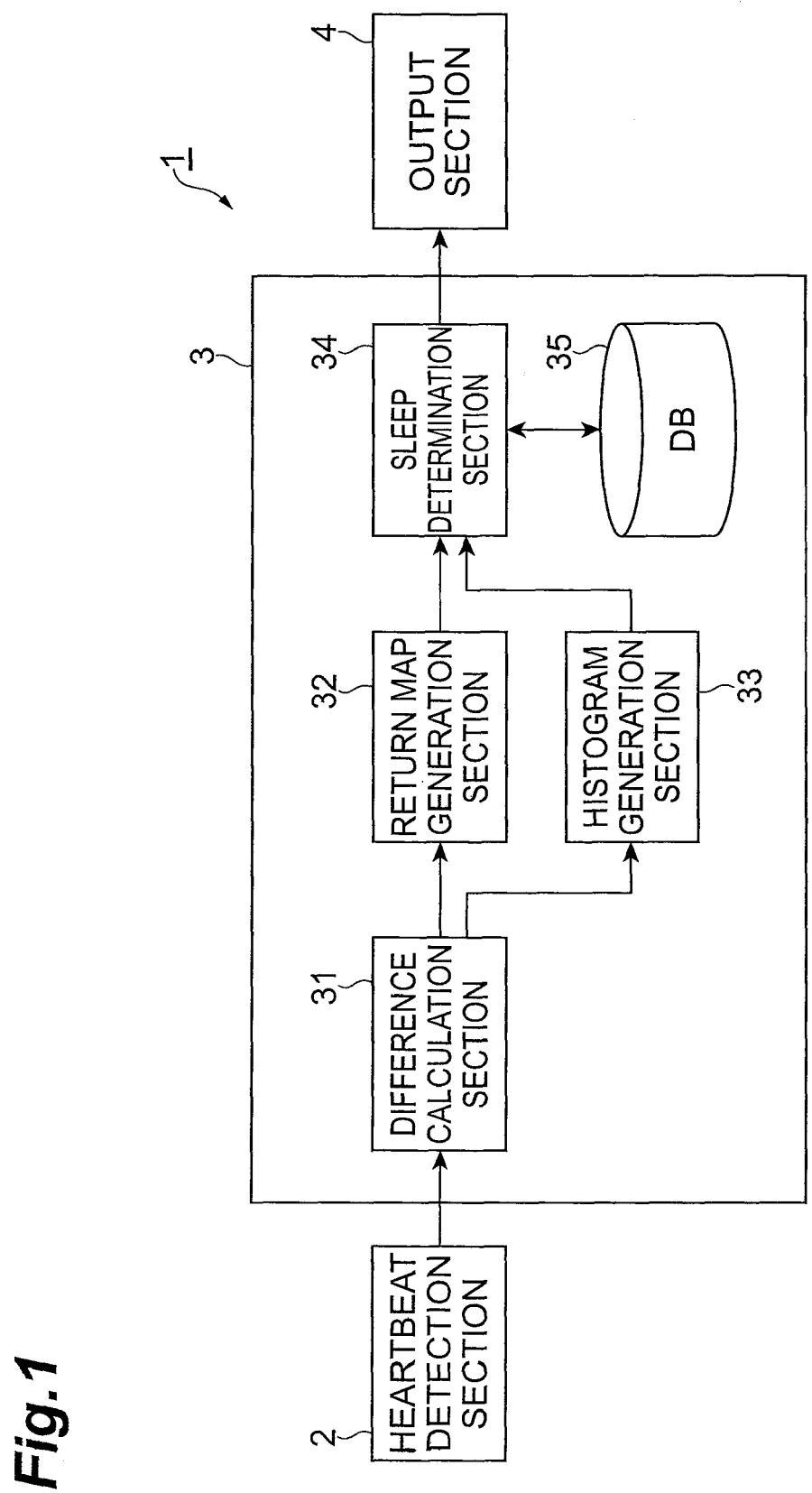
FIG. 1 is a schematic configuration diagram of a sleep determination device according to an embodiment of the present invention.

REFERENCE SIGNS LIST 1 sleep determination device
2 heartbeat detection section
3 ECU
4 output section
31 difference calculation section
32 return map generation section
33 histogram generation section
34 sleep determination section
35 database

DESCRIPTION OF EMBODIMENTS

An embodiment of the present invention will be described in detail with reference to the accompanied drawings. In the explanation of the drawings, the same symbols are attached to the same components and duplicated description thereof will be omitted.

FIG. 1 is a schematic configuration diagram of a sleep determination device according to the present embodiment.

As shown in FIG. 1, a sleep determination device 1 according to the present embodiment is a device to determine a sleep state of a subject and installed, for example, in a vehicle and applied to determination of a sleep stage, that is, a level of sleep depth (sleep level) of a driver, who is a subject sleeping quietly in a parking lot etc.

The sleep determination device 1 is configured to comprise, for example, a heartbeat detection section 2, an ECU (Electronic Control Unit) 3, and an output section 4. The heartbeat detection section 2 functions as a heartbeat obtaining unit that obtains a heartbeat of the subject and such one is used, which detects a small current corresponding to a heartbeat like an electrode section used in, for example, an electrocardiograph tester. As the heartbeat detection section 2, any one may be used as long as it can detect a heartbeat state, such as an electrocardiographic waveform, of a subject. When detecting a heartbeat state of a driver of a vehicle, it is preferable to install the heartbeat detection section 2 in, for example, the driver's seat.

The ECU 3 controls the whole of the sleep determination device 1 and is configured by, for example, a computer including a CPU, ROM, and RAM, as a main component. The ECU 3 includes a difference calculation section 31, a return map generation section 32, a histogram generation section 33, a sleep determination section 34, and a database 35.

The difference calculation section 31 functions as a difference calculating unit that calculates a heartbeat cycle for each heartbeat based on a heartbeat signal output from the heartbeat detection section 2, and calculates difference values until Nth-degree difference values set in advance are obtained, with difference values between the successive heartbeat cycles as first-degree difference values and difference values between the successive first-degree difference values as second-degree difference values.

Figure 2:
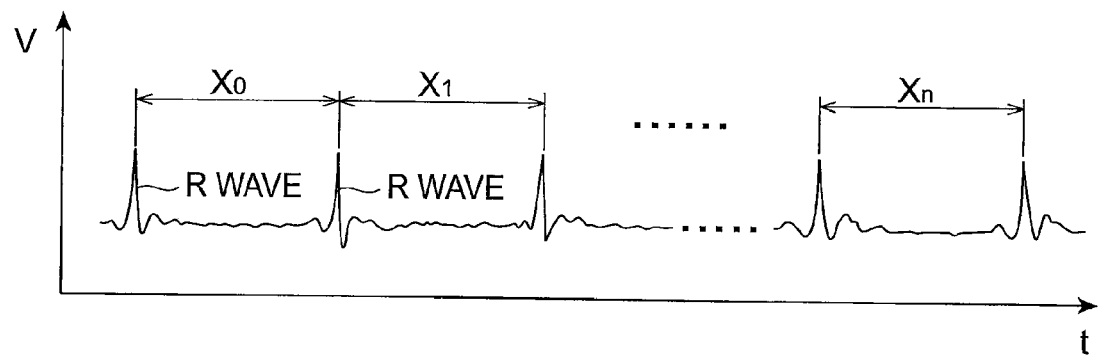
FIG. 2 is an explanatory diagram of a heartbeat signal.

For example, as shown in FIG. 2, a time X (RRI) between successive R waves in the heartbeat signal of a subject is calculated as a single heartbeat cycle and heartbeat cycles $X0, X1, \ldots, Xn$ are calculated successively. Then, as difference values between the successive heartbeat cycles, first-degree difference values $X0^{(1)}, X1^{(1)} \ldots$ are calculated, as difference values between the successive first-degree difference values, second-degree difference values $X0^{(2)}, X1^{(2)} \ldots$ are calculated and the calculation is performed until Nth-degree difference values $X0^{(N)}, X1^{(N)} \ldots$ set in advance are obtained.

The difference value $Xk^{(N)}$ of the heartbeat cycle is calculated by the following expression (1).

$$Xk^{(N)} = Xk+1^{(N-1)} - Xk^{(N-1)} \tag{1}$$

$Xk+1^{(N-1)}$ and $Xk^{(N-1)}$ are difference values successive with respect to time of the (N−1)th-degree difference values. As a difference between $Xk+1^{(N-1)}$ and $Xk^{(N-1)}$, $Xk^{(N)}$ is calculated.

Figure 3:
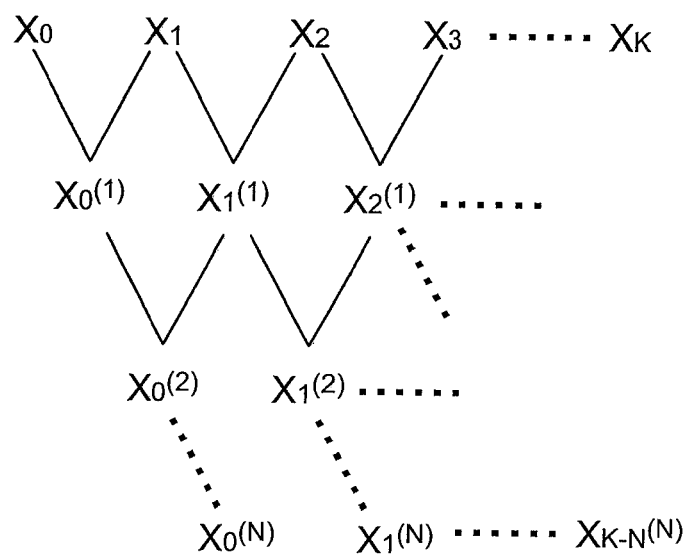
FIG. 3 is an explanatory diagram of heartbeat cycles and difference values calculated by the sleep determination device in FIG. 1.

FIG. 3 shows an explanatory diagram of heartbeat cycles and difference values between successive heartbeat cycles.

As shown in FIG. 3, each time a heartbeat signal is input, the heartbeat cycle Xk is calculated and the first-degree difference value $Xk-1^{(1)}$ to the Nth-degree difference value $Xk-N^{(N)}$ are calculated using the expression (1). For example, when X0 is 1.0 s (second) and X1 is 1.2 s, the first-degree difference value $X0^{(1)}$ between both is 0.2 s. The second-degree difference value $X0^{(2)}$ is calculated as a difference between the first-degree difference value $X0^{(1)}$ and the first-degree difference value $X1^{(1)}$.

The return map generation section 32 functions as a map generating unit that generates a return map that uses as parameters two values successive with respect to time of the heartbeat cycles and the difference values from the first-degree difference values to the Nth-degree difference values.

Figure 4:
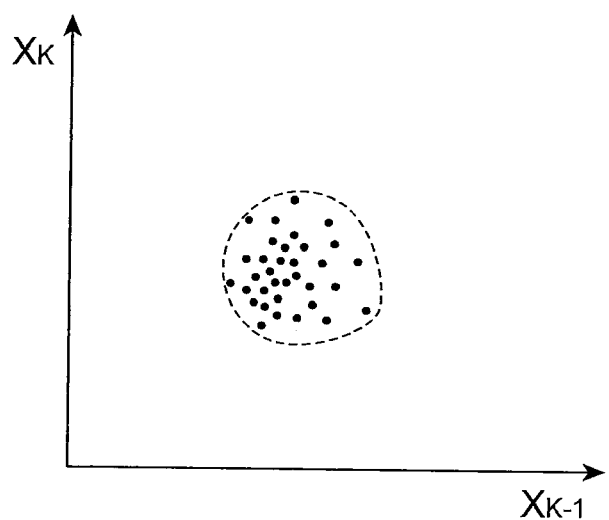
FIG. 4 is an explanatory diagram of a return map generated by the sleep determination device in FIG. 1.

FIG. 4 shows an example in which a return map of the heartbeat cycles (0th-degree difference values) with Xk−1 and Xk as its parameters is generated. For example, by representing the value of Xk−1 on the horizontal axis and the value of Xk on the vertical axis and by plotting data, a return map of the heartbeat cycles is generated. At this time, it is only required to generate a return map as to the heartbeat cycles in a predetermined period of time (for example, a measurement time of 30 seconds) set in advance. In this manner, a return map that uses as parameters successive values of the difference values is generated also for each of the difference values from the first-degree difference values to the Nth-degree difference values.

Figure 5:
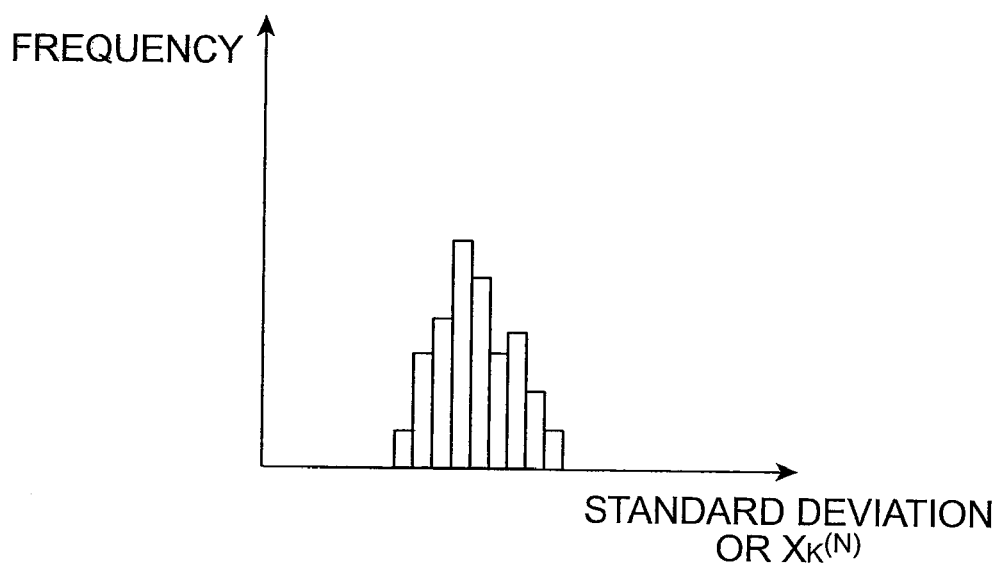
FIG. 5 is an explanatory diagram of a histogram generated by the sleep determination device in FIG. 1.

The histogram generation section 33 functions as a histogram generating unit that generates histograms of the heartbeat cycles and the difference values from the first-degree difference values to the Nth-degree difference values. For example, as shown in FIG. 5, by representing the standard deviation or $Xk^{(N)}$ for each predetermined period of time (for example, 30 seconds) on the horizontal axis and the frequency on the vertical axis, histograms of the heartbeat cycle data and the difference value data in a predetermined period of time (for example, a measurement time of 10 minutes) set in advance are generated, respectively.

The return map and histogram of the heartbeat cycles and difference values are generated for all of the heartbeat cycles and difference values in some cases, or only those which are set in advance are generated in some cases.

The sleep determination section 34 functions as a sleep determining unit that determines a sleep stage of a subject based on the distribution data generated, that is, the return map and the histogram by referring to distribution data for determination for each sleep stage set in advance. As the sleep stage, for example, five stages S0 to S4 are set.

The determination of a sleep stage of the subject using the return map is made by comparing the return map generated based on the heartbeat state of the subject with a return map for determination set in advance for each sleep stage.

For example, for any of the heartbeat cycles and the first-degree difference values to the Nth-degree difference values, a return map for determination is generated based on the heartbeat signal the sleep stage of which is known in advance, and the sleep stage of the subject is determined by comparing the return map for determination with the return map on the basis of the heartbeat state of the subject.

Figure 6:
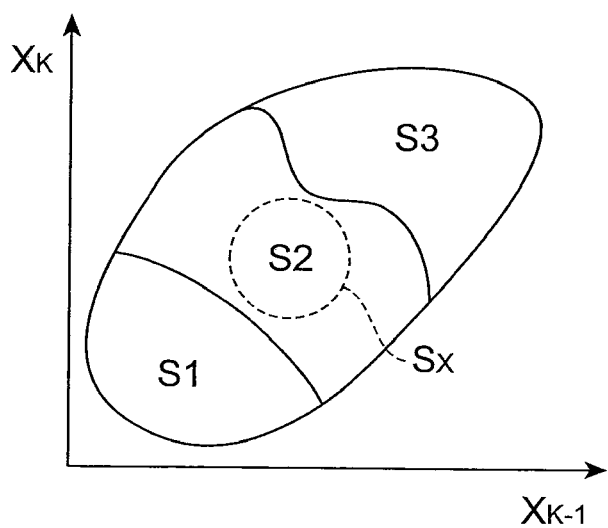
FIG. 6 is an explanatory diagram of a return map for determination used for sleep determination by the sleep determination device in FIG. 1.

FIG. 6 shows an example of a return map for determination.

The return map for determination in FIG. 6 shows an example in which a return map of the heartbeat cycles (0th-degree difference values) with Xk−1, Xk as parameters is generated. For example, this is used to determine the sleep stages S1 to S3 of the sleep stages S0 to S4 when the horizontal axis represents the value of Xk−1 and the vertical axis represents the value of Xk. The regions S1 to S3 in the return map in FIG. 6 are set by the regions formed when calculating the heartbeat cycle based on the heartbeat signal the sleep stage of which is known in advance and plotting it on the return map. The sleep stages S0 and S4 may be determined by a return map set separately from that in FIG. 6.

When the return map for determination in FIG. 6 and the return map on the basis of the heartbeat signal of the subject are compared and if a data region Sx of the return map on the basis of the heartbeat signal in, for example, a predetermined period of time (for example, 30 seconds) of the subject, is included in the region S2, the sleep stage of the subject is determined to be S2.

On the other hand, when the data region Sx of the return map on the basis of the heartbeat signal in a predetermined period of time (for example, 30 seconds) of the subject is included in both S2 and S3, it is preferable to determine the sleep stage using a return map for discrimination to discriminate between the sleep stages S2 and S3.

Figure 7:
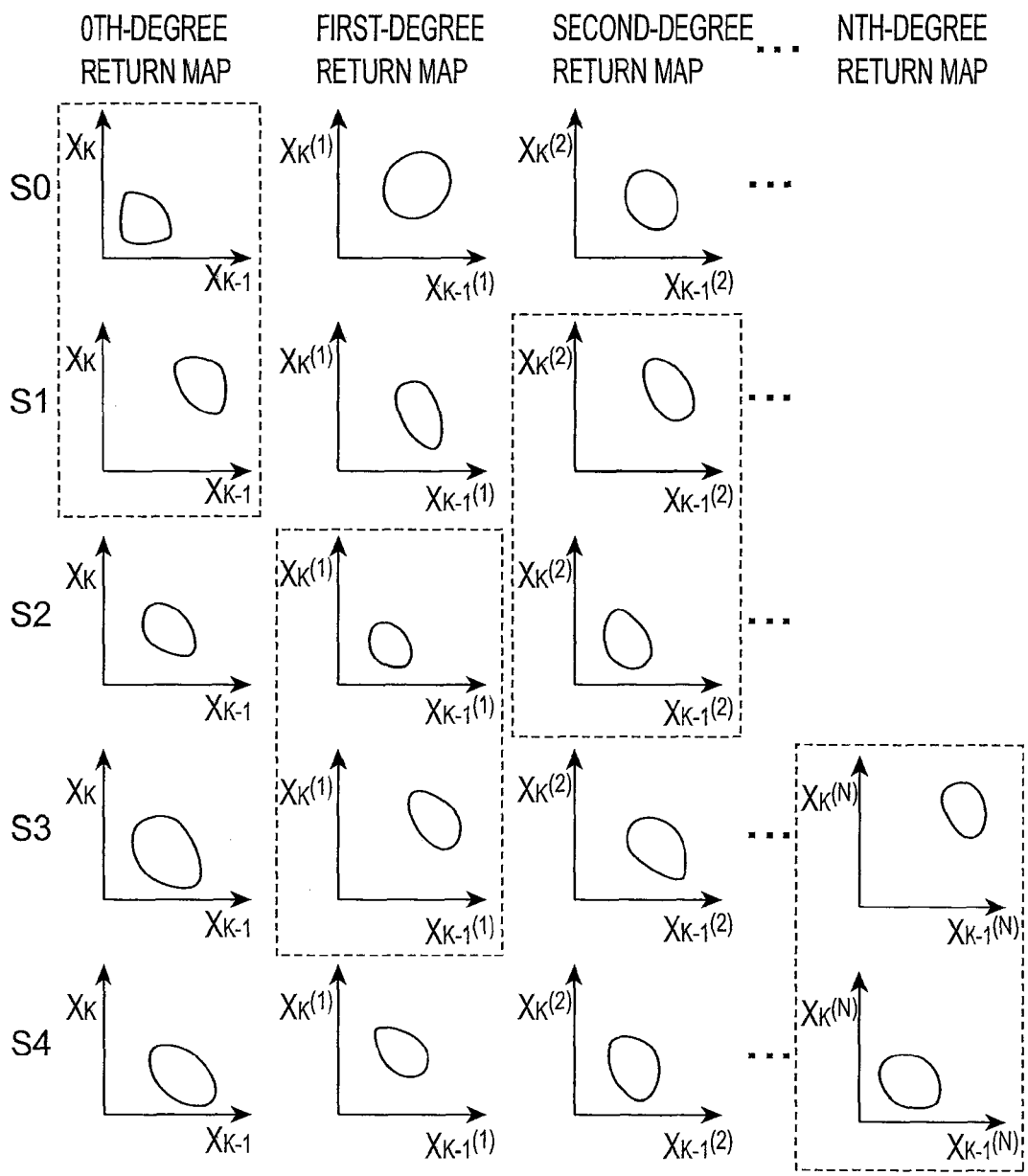
FIG. 7 is an explanatory diagram of return maps for discrimination used for sleep determination by the sleep determination device in FIG. 1.

As shown in FIG. 7, by the use of the heartbeat signal (teacher signal) the sleep stage of which is known in advance, a 0th-degree return map of the heartbeat cycles, a first-degree return map of the first-degree difference values, a second-degree return map of the second-degree difference values, ..., and an Nth-degree return map of the Nth-degree difference values are generated and a return map in which the degree of separation between the sleep stages S0 and S1 is high, a return map in which the degree of separation between S1 and S2 is high, a return map in which the degree of separation between S2 and S3 is high, and a return map in which the degree of separation between S3 and S4 is high are selected as a return map for discrimination, respectively. As a method of selecting a return map, it is recommended to select, for example, a return map in which the data regions are most distant from each other in the return map of the neighboring sleep stages.

In FIG. 7, as a return map for discrimination between the sleep stages S0 and S1, S0 and S1 of the 0th-degree return map are set, as a return map for discrimination between the sleep stages S1 and S2, S1 and S2 of the second-degree return map are set, as a return map for discrimination between the sleep stages S2 and S3, S2 and S3 of the first-degree return map are set, and as a return map for discrimination between the sleep stages S3 and S4, S3 and S4 of the Nth-degree return map are set. The circular region in the return map in FIG. 7 represents a data region.

Then, by the use of the return map for discrimination of the sleep stages to be discriminated, a return map for discrimination to which the return map on the basis of the heartbeat signal of the subject is more approximate is extracted and the sleep stage of the extracted return map for discrimination is determined to be the sleep stage of the subject.

In the return map for determination, when a data region is present in a region other than the region of the sleep stage, it is preferable to determine that the data of the subject is abnormal. Hence, it is possible to prevent an erroneous sleep stage of the subject from being determined.

On the other hand, the determined of a sleep stage of a subject using a histogram is made by comparing the histogram generated based on the heartbeat state of the subject with a histogram for determination set in advance for each sleep stage.

For example, for any of the heartbeat cycles and the first-degree difference values to the Nth-degree difference values, a histogram for determination is generated based on the heartbeat signal the sleep stage of which is known in advance, and the sleep stage of the subject is determined by comparing the histogram for determination with the histogram on the basis of the heartbeat state of the subject.

When it is difficult to determine the sleep stage even by using the histogram based on the heartbeat signal of the subject and the histogram for determination, it is preferable to determine the sleep stage using a return map for discrimination to discriminate between the sleep stages.

Figure 8:
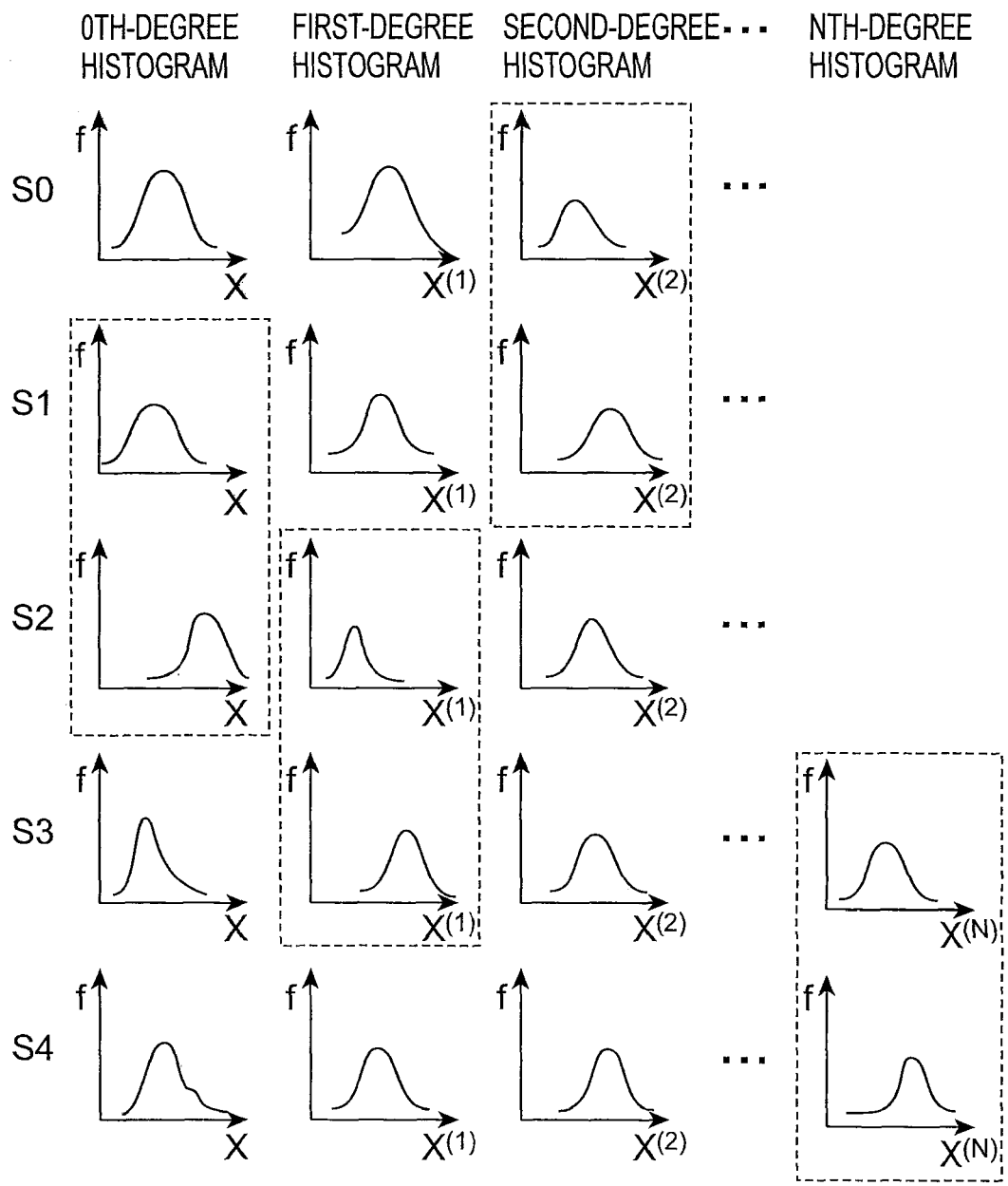
FIG. 8 is an explanatory diagram of histograms for discrimination used for sleep determination by the sleep determination device in FIG. 1.

For example, as shown in FIG. 8, by the use of the heartbeat signal the sleep stage of which is known in advance, a 0th-degree histogram of the heartbeat cycles, a first-degree histogram of the first-degree difference values, a second-degree histogram of the second-degree difference values, ..., and an Nth-degree histogram of the Nth-degree difference values are generated and a histogram in which the degree of separation between the sleep stages S0 and S1 is high, a histogram in which the degree of separation between S1 and S2 is high, a histogram in which the degree of separation between S2 and S3 is high, and a histogram in which the degree of separation between S3 and S4 is high are selected as a histogram for discrimination, respectively. As a method of selecting a histogram, it is recommended to select, for example, a histogram in which the data regions are most distant from each other in the histogram of the neighboring sleep stages.

In FIG. 8, as a histogram for discrimination between the sleep stages S0 and S1, S0 and S1 of the second-degree histogram are set, as a histogram for discrimination between the sleep stages S1 and S2, S1 and S2 of the 0th-degree histogram are set, as a histogram for discrimination between the sleep stages S2 and S3, S2 and S3 of the first-degree histogram are set, and as a histogram for discrimination between the sleep stages S3 and S4, S3 and S4 of the Nth-degree histogram are set. Each histogram in FIG. 8 approximately represents a histogram in the shape of a bar graph by a curved line. The histogram used in FIG. 8 may be one in the shape of a bar graph.

Then, by the use of the histogram for discrimination of the sleep stages to be discriminated, a histogram for discrimination to which the histogram on the basis of the heartbeat signal of the subject is more approximate is extracted and the sleep stage of the extracted histogram for discrimination is determined to be the sleep stage of the subject.

In the histogram for determination, when a data region is present in a region other than the region of the sleep stage, it is preferable to determine that the data of the subject is abnormal. Hence, it is possible to prevent an erroneous sleep stage of the subject from being determined.

It may also be possible to determine the sleep stage of the subject using both the return map and the histogram.

For example, as to the return map and the histogram generated based on the heartbeat signal of the subject, the sleep stage of the subject is determined using the return map for determination and the histogram for determination. At this time, when it is difficult to determine a sleep stage from neighboring sleep stages, such as when it is difficult to determine a sleep stage to be S1 or S2, the sleep stage of the subject is determined using the return map for discrimination and the histogram for discrimination.

At this time, it is preferable to discriminate between the sleep stages of the subject using the return map for discrimination or the histogram for discrimination used for discrimination in which the degree of separation between the sleep stages is higher. For example, when the degree of separation between the sleep stages in the return map for discrimination is 90% and the degree of separation between the sleep stages in the histogram for discrimination is 70%, the sleep stage of the subject is discriminated using the return map for discrimination in which the degree of separation is higher.

In FIG. 1, the database 35 functions as a recording unit that records data for sleep stage determination, such as the return map for determination, the histogram for determination, the return map for discrimination, and the histogram for discrimination. The output section 4 outputs a sleep stage of a subject determined by the ECU 3 and a display monitor etc. is used.

Next, the operation of the sleep determination device according to the present embodiment and a sleep determination method according to the present embodiment will be described.

Figure 9:
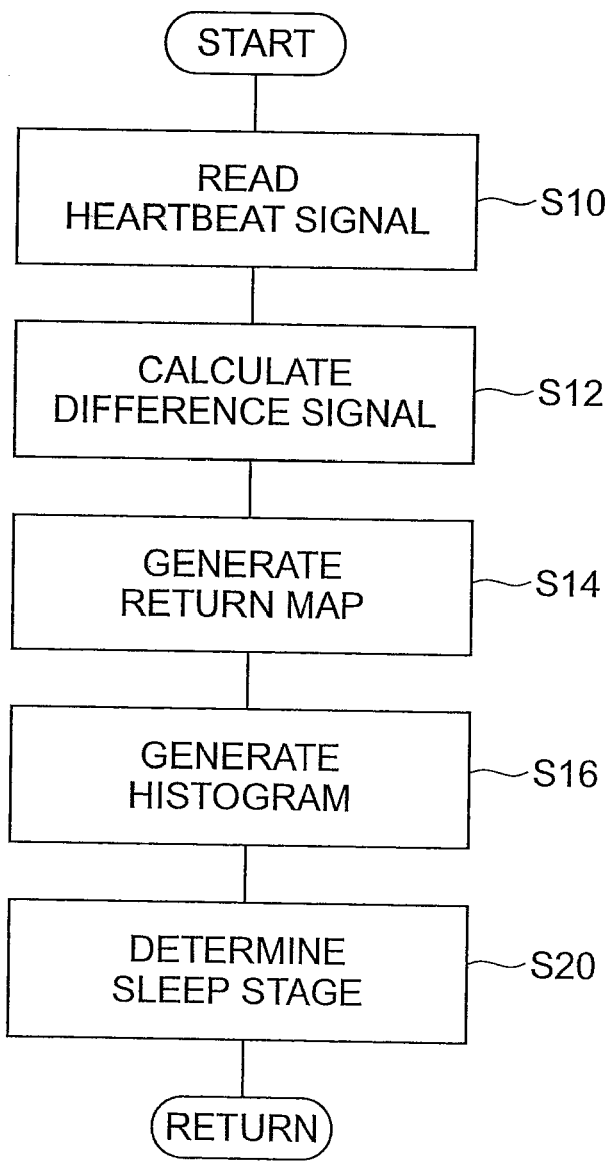
FIG. 9 is a flowchart showing operations of the sleep determination device in FIG. 1 and a sleep determination method according to the present embodiment.

FIG. 9 is a flowchart showing the operation of the sleep determination device according to the present embodiment and the sleep determination method according to the present embodiment. The control processing in FIG. 9 is performed repeatedly in a predetermined cycle by, for example, the ECU 3.

First, as shown in S10 in FIG. 9, processing to read a heartbeat signal is performed. The processing to read a heartbeat signal is processing to read a heartbeat signal of a subject output from the heartbeat detection section 2. The heartbeat signal is input in a waveform that repeatedly produces an R wave in accordance with the heartbeat as shown in FIG. 2.

Then, the process moves to S12 and processing to calculate a difference signal is performed. The processing to calculate a difference signal is processing to calculate a heartbeat cycle for each heartbeat based on the heartbeat signal, and calculate difference values until obtaining Nth-degree difference values set in advance with difference values between the successive heartbeat cycles as first-degree difference values and difference values between the successive first-degree difference values as second-degree difference values.

For example, the heartbeat cycle is calculated as a time between the R waves detected repeatedly by detecting the R wave from the heartbeat signal. Then, as shown in FIG. 3, when the heartbeat cycles $X0, X1, \ldots, Xk$ are calculated, as difference values between the successive heartbeat cycles, the first-degree difference values $X0^{(1)}, X1^{(1)} \ldots$ are calculated, as difference values between the successive first-degree difference values, the second-degree difference values $X0^{(2)}$, $X1^{(2)} \ldots$ are calculated and the calculation is performed until the Nth-degree difference values $X0^{(N)}, X1^{(N)} \ldots$ are obtained. The difference value $Xk^{(N)}$ of the heartbeat cycle is calculated by the above-described expression (1).

Then, the process moves to S14 in FIG. 9 and processing to generate a return map is performed. The processing to generate a return map is processing to generate a return map that uses as parameters two difference values successive with respect to time of the heartbeat cycles and the difference values from the first-degree difference values to the Nth-degree difference values. For example, as shown in FIG. 4, a return map of the heartbeat cycles (0th-degree difference values) that uses $Xk-1$, $Xk$ as parameters is generated and similarly, a return map of the first-degree difference values that uses $Xk-1^{(1)}$, $Xk^{(1)}$ as parameters is generated, a return map of the second-degree difference values that uses $Xk-1^{(2)}$, $Xk^{(2)}$ as parameters is generated, and return maps of up to the Nth-degree difference values are generated.

In the processing to generate a return map, in some cases, only the return map necessary to determine a sleep stage of a subject is generated of the return maps of the heartbeat cycles and the first-degree difference values to the Nth-degree difference values instead of generating all of the return maps of the heartbeat cycles and the first-degree difference values to the Nth-degree difference values.

Then, the process moves to S16 and processing to generate a histogram is performed. The processing to generate a histogram is processing to generate a histogram of the heartbeat cycles and the difference values from the first-degree difference values to the Nth-degree difference values. For example, as shown in FIG. 5, a histogram of the heartbeat cycles (0th-degree difference values) detected in a predetermined period of time is generated and the histograms of the first-degree difference values to the Nth-degree difference values detected in a predetermined period of time are generated.

In the processing to generate a histogram, in some cases, only the histogram necessary to determine a sleep stage of a subject is generated of the histograms of the heartbeat cycles and the first-degree difference values to the Nth-degree difference values instead of generating all of the histograms of the heartbeat cycles and the first-degree difference values to the Nth-degree difference values.

Then, the process moves to S20 and processing to determine a sleep stage is performed. The processing to determine a sleep stage is processing to determine a sleep stage of a subject. Processing to determine a sleep stage includes determination processing using only a return map, determination processing using only a histogram, and determination processing using a return map and a histogram.

First, in the determination processing using only a return map, a sleep stage of the subject is determined by comparing the return map generated based on the heartbeat state of the subject with the return map for determination set in advance for each sleep stage.

For example, for any of the heartbeat cycles and the first-degree difference values to the Nth-degree difference values, the sleep stage of the subject is determined by generating a return map for determination based on the heartbeat signal the sleep stage of which is known in advance and comparing the return map for determination with the return map on the basis of the heartbeat state of the subject.

For example, the determination of the sleep stages S1 to S3 is made by using the return map for determination as shown in FIG. 6 and determining the sleep stage depending on whether or not the data region Sx of the return map of the heartbeat signal of the subject is included in the sleep stages S1 to S3. The determination of the sleep stages S0 and S4 may be made using a return map set separately from that in FIG. 6.

As shown in FIG. 6, when the data region Sx of the return map on the basis of the heartbeat signal of the subject is included in the region S2, the sleep stage of the subject is determined to be S2.

On the other hand, when the data region Sx of the return map on the basis of the heartbeat signal of the subject is included in both S2 and S3, it is preferable to determine the sleep stage using a return map for discrimination to discriminate between the sleep stages S2 and S3.

As shown in FIG. 7, by the use of the heartbeat signal (teacher signal) the sleep stage of which is known in advance, a 0th-degree return map of the heartbeat cycles, a first-degree return map of the first-degree difference values, a second-degree return map of the second-degree difference values, . . . , and an Nth-degree return map of the Nth-degree difference values are generated and a return map in which the degree of separation between the sleep stages S0 and S1 is high, a return map in which the degree of separation between S1 and S2 is high, a return map in which the degree of separation between S2 and S3 is high, and a return map in which the degree of separation between S3 and S4 is high are selected as a return map for discrimination, respectively. As a method of selecting a return map, it is recommended to select, for example, a return map in which the data regions are most distant from each other in the return map of the neighboring sleep stages. The horizontal axis Xk−1 and the vertical axis Xk of the 0th-degree return map in FIG. 7 represent the heartbeat cycle value and the horizontal axis Xk−1 and the vertical axis Xk of the first-degree to the Nth-degree return maps represent the first-degree to the Nth-degree difference values In FIG. 7, as a return map for discrimination between the sleep stages S0 and S1, S0 and S1 of the 0th-degree return map are set, as a return map for discrimination between the sleep stages S1 and S2, S1 and S2 of the second-degree return map are set, as a return map for discrimination between the sleep stages S2 and S3, S2 and S3 of the first-degree return map are set, and as a return map for discrimination between the sleep stages S3 and S4, S3 and S4 of the Nth-degree return map are set.

Then, by the use of the return map for discrimination of the sleep stages to be discriminated, a return map for discrimination to which the return map on the basis of the heartbeat signal of the subject is more approximate is extracted and the sleep stage of the extracted return map for discrimination is determined to be the sleep stage of the subject.

In the return map for determination, when a data region is present in a region other than the region of the sleep stage, it is preferable to determine that the data of the subject is abnormal. Hence, it is possible to prevent an erroneous sleep stage of the subject from being determined.

When the sleep determination is made using only a return map without a histogram, the processing to generate a histogram in S16 may be omitted.

Next, in the determination processing using only a histogram, the sleep stage of the subject is determined by comparing the histogram generated based on the heartbeat state of the subject with the histogram for determination set in advance for each sleep stage.

For example, for any of the heartbeat cycles and the first-degree difference values to the Nth-degree difference values, a histogram for determination is generated based on the heartbeat signal the sleep stage of which is known in advance, and the sleep stage of the subject is determined by comparing the histogram for determination with the histogram on the basis of the heartbeat state of the subject.

When it is difficult to determine the sleep stage even by using the histogram on the basis of the heartbeat signal of the subject and the histogram for determination, it is preferable to determine a sleep stage using a return map for discrimination to discriminate between the sleep stages.

For example, as shown in FIG. 8, by the use of the heartbeat signal (teacher signal) the sleep stage of which is known in advance, a 0th-degree histogram of the heartbeat cycles, a first-degree histogram of the first-degree difference values, a second-degree histogram of the second-degree difference values, . . . , and an Nth-degree histogram of the Nth-degree difference values are generated and a histogram in which the degree of separation between the sleep stages S0 and S1 is high, a histogram in which the degree of separation between S1 and S2 is high, a histogram in which the degree of separation between S2 and S3 is high, and a histogram in which the degree of separation between S3 and S4 is high are selected as a histogram for discrimination, respectively. As a method of selecting a histogram, it is recommended to select, for example, a histogram in which the data regions are most distant from each other in the histogram of the neighboring sleep stages. The horizontal axis of the 0th-degree histogram in FIG. 8 represents the heartbeat cycle value and the vertical axis represents a frequency f. The horizontal axes $X^{(1)}$ to $X^{(N)}$ of the first-degree to the Nth-degree histograms in FIG. 8 represent the first-degree to the Nth-degree difference values and the vertical axis Xk represents the frequency f.

In FIG. 8, as a histogram for discrimination between the sleep stages S0 and S1, S0 and S1 of the second-degree histogram are set, as a histogram for discrimination between the sleep stages S1 and S2, S1 and S2 of the 0th-degree histogram are set, as a histogram for discrimination between the sleep stages S2 and S3, S2 and S3 of the first-degree histogram are set, and as a histogram for discrimination between the sleep stages S3 and S4, S3 and S4 of the Nth-degree histogram are set.

Then, by the use of the histogram for discrimination of the sleep stages to be discriminated, a histogram for discrimination to which the histogram on the basis of the heartbeat signal of the subject is more approximate is extracted and the sleep stage of the extracted histogram for discrimination is determined to be the sleep stage of the subject.

In the histogram for determination, when a data region is present in a region other than the region of the sleep stage, it is preferable to determine that the data of the subject is abnormal. Hence, it is possible to prevent an erroneous sleep stage of the subject from being determined.

When the sleep determination is made using only a histogram without a return map, the processing to generate a histogram in S14 may be omitted.

Next, when the sleep stage of a subject is determined using both the return map and the histogram, as to the return map and the histogram generated based on the heartbeat signal of the subject, the sleep stage of the subject is determined using the return map for determination and the histogram for determination. At this time, when it is difficult to determine a sleep stage from neighboring sleep stages, such as when it is difficult to determine a sleep stage to be S1 or S2, the sleep stage of the subject is determined using the return map for discrimination and the histogram for discrimination.

At this time, it is preferable to discriminate between the sleep stages of a subject using the return map for discrimination or the histogram for discrimination used for discrimination in which the degree of separation between the sleep stages is higher. For example, when the degree of separation between the sleep stages in the return map for discrimination is 90% and the degree of separation between the sleep stages in the histogram for discrimination is 70%, the sleep stage of the subject is discriminated using the return map for discrimination in which the degree of separation is higher.

In this case, as the degree of separation, for example, when an overlap region of the data regions of the return maps for discrimination with different sleep stages is 10%, the degree of separation is determined to be 90% and when the overlap region is 30%, the degree of separation is determined to be 70%. The degree of separation may be set by another technique. When the processing in S20 in FIG. 9 is completed, a series of control processing is completed.

As described above, the sleep determination device and the sleep determination method according to the present embodiment calculate a heartbeat cycle for each heartbeat of a subject, calculate difference values until obtaining Nth-degree difference values set in advance with difference values between the successive heartbeat cycles as first-degree difference values and difference values between the successive first-degree difference values as second-degree difference values, generate distribution data indicative of the distribution of the respective values of the heartbeat cycles and the difference values from the first-degree difference values to the Nth-degree difference values, and determine a sleep stage of the subject based on the distribution data generated by the distribution data generating unit by referring to the distribution data for determination set in advance for each sleep stage. Hence, it is possible to discriminate between sleep stages of the subject in consideration of not only the fluctuation state of heartbeat cycles of the subject but also the fluctuation state of the fluctuation state etc. Therefore, it is possible to precisely determine a sleep stage of the subject based on its heartbeat information. Further, it is possible to determine the sleep stage of the subject in real time by updating data of the heartbeat cycles and the difference values each time the heartbeat signal is received.

It is also possible to precisely discriminate between sleep stages of the subject based on the heartbeat cycle of the subject and the temporal change of the fluctuation state thereof etc, by generating a return map that uses as parameters two successive values of the heartbeat cycles and the difference values of the first-degree difference values to the Nth-degree difference values calculated by the difference calculation section 31 and by comparing the generated return map with the return map for determination set in advance for each sleep stage to determine the sleep stage of the subject.

It is also possible to precisely discriminate between sleep stages of a subject by setting a return map for discrimination in advance in which the degree of separation is high in neighboring sleep stages and comparing the return map generated by the distribution data generating unit with the return map for discrimination to determine the sleep stage of the subject.

It is also possible to precisely discriminate between sleep stages of a subject in consideration of statistical data, such as the heartbeat cycle of the subject and the fluctuation state thereof etc. by generating histograms of the heartbeat cycles and the difference values from the first-degree difference values to the Nth-degree difference values calculated by the difference calculation section 31 and comparing the generated histogram with the histogram for determination set in advance for each sleep stage to determine the sleep stage of the subject.

It is also possible to precisely discriminate between sleep stages of a subject and to accurately determine a sleep stage by discriminating between the sleep stages of the subject by using a return map or a histogram in which the degree of separation is higher.

It is also possible to precisely discriminate between sleep stages of a subject by setting a histogram for discrimination in advance in which the degree of separation is high in neighboring sleep stages as a histogram for determination and comparing the histogram generated by the distribution data generating unit with the histogram for discrimination to determine the sleep stage of the subject.

In the above-described embodiment, the embodiment of the sleep determination device and the sleep determination method according to the present invention is explained and the sleep determination device and the sleep determination method according to the present invention are not limited to those described in the present embodiment. The sleep determination device and the sleep determination method according to the present invention may be modified to a sleep determination device according to an embodiment without altering the gist described in each claim or may be one to which the sleep determination device and the sleep determination method according to the present invention are applied.

For example, in the embodiment, the case where the subject is a driver of a vehicle is explained, however, the subject may be one other than the driver and one who is not in the vehicle. Further, the present invention may be applied to medical equipment or bedding etc.

INDUSTRIAL APPLICABILITY

According to the present invention, it is possible to precisely determine a sleep stage based on heartbeat information of a subject.

The invention claimed is:
1. A sleep determination device comprising:
a heartbeat obtaining unit that obtains a heartbeat of a subject;
a difference calculating unit that calculates a heartbeat cycle for each heartbeat based on the heartbeat obtained by the heartbeat obtaining unit, and calculates difference values until obtaining Nth-degree difference values set in advance with difference values between the successive heartbeat cycles as first-degree difference values and difference values between the successive first-degree difference values as second-degree difference values;
a distribution data generating unit that generates distribution data indicative of a distribution of the respective values in a predetermined period of time for each of the heartbeat cycles and the difference values from the first- degree difference values to the Nth-degree difference values calculated by the difference calculating unit; and a sleep determining unit that determines a sleep stage of the subject based on the distribution data generated by the distribution data generating unit by referring to distribution data for determination set in advance for each sleep stage.

2. The sleep determination device according to claim 1, wherein the distribution data generating unit generates a return map that uses as parameters successive values of the heartbeat cycles and the difference values in a predetermined period of time for each of the heartbeat cycles and the difference values from the first-degree difference values to the Nth-degree difference values calculated by the difference calculating unit; and the sleep determining unit compares the return map generated by the distribution data generating unit with a return map for determination set in advance for each sleep stage to determine a sleep stage of the subject.

3. The sleep determination device according to claim 2, wherein the sleep determining unit sets a return map for discrimination in advance in which the degree of separation is high in neighboring sleep stages and compares the return map generated by the distribution data generating unit with the return map for discrimination to determine a sleep stage of the subject.

4. The sleep determination device according to claim 1, wherein the distribution data generating unit generates a histogram for each of the heartbeat cycles and the first-degree difference values to the Nth-degree difference values calculated by the difference calculating unit, and the sleep determining unit compares the histogram generated by the distribution data generating unit with a histogram for determination set in advance for each sleep stage to determine a sleep stage of the subject.

5. The sleep determination device according to claim 4, wherein the sleep determining unit sets a histogram for discrimination in advance in which the degree of separation is high in neighboring sleep stages and compares the histogram generated by the distribution data generating unit with the histogram for discrimination to determine a sleep stage of the subject.

6. A sleep determination method comprising:

a heartbeat obtaining step of obtaining a heartbeat of a subject;

a difference calculating step of calculating a heartbeat cycle for each heartbeat based on the heartbeat obtained in the heartbeat obtaining step, and calculating difference values until obtaining Nth-degree difference values set in advance with difference values between the successive heartbeat cycles as first-degree difference values and difference values between the successive first-degree difference values as second-degree difference values;

a distribution data generating step of generating distribution data indicative of a distribution of the respective values in a predetermined period of time for each of the heartbeat cycles and the difference values from the first-degree difference values to the Nth-degree difference values calculated in the difference calculating step; and a sleep determining step of determining a sleep stage of the subject based on the distribution data generated in the distribution generating step by referring to distribution data for determination set in advance for each sleep stage.

7. The sleep determination method according to claim 6, wherein the distribution data generating step generates a return map that uses as parameters successive values of the heartbeat cycles and the difference values in a predetermined period of time for each of the heartbeat cycles and the difference values from the first-degree difference values to the Nth-degree difference values calculated in the difference calculating step, and the sleep determining step compares the return map generated in the distribution data generating step with a return map for determination set in advance for each sleep stage to determine a sleep stage of the subject.

8. The sleep determination method according to claim 7, wherein the sleep determining step sets a return map for discrimination in advance in which the degree of separation is high in neighboring sleep stages, and compares the return map generated in the distribution data generating step with the return map for discrimination to determine a sleep stage of the subject.

9. The sleep determination method according to claim 6, wherein the distribution data generating step generates a histogram for each of the heartbeat cycles and the first-degree difference values to the Nth-degree difference values calculated by the difference calculating unit, and the sleep determining step compares the histogram generated in the distribution data generating step with a histogram for determination set in advance for each sleep stage to determine a sleep stage of the subject.

10. The sleep determination method according to claim 9, wherein the sleep determining step sets a histogram for discrimination in advance in which the degree of separation is high in neighboring sleep stages, and compares the histogram generated by the distribution data generating unit with the histogram for discrimination to determine a sleep stage of the subject.

* * * * *